United States Patent
Cary et al.

Patent Number: 5,129,949
Date of Patent: Jul. 14, 1992

[54] HERBICIDAL COMPOSITION AND METHOD FOR SAFENING HERBICIDES IN CEREAL CROPS USING 1-CARBETHOXYETHYL-3,6-DICHLORO-2-METHOXYBENZOATE

[75] Inventors: Gail E. Cary; Dale L. Shaner, both of Lawrenceville, N.J.

[73] Assignee: American Cyanamid Company, Stamford, Conn.

[21] Appl. No.: 733,509

[22] Filed: Jul. 22, 1991

[51] Int. Cl.$^5$ .................... A01N 37/10; A01N 43/40; A01N 43/50

[52] U.S. Cl. ........................................ 71/107; 71/92; 71/94

[58] Field of Search ............... 71/92, 94, 107

[56] References Cited

U.S. PATENT DOCUMENTS

| | | | |
|---|---|---|---|
| 4,388,473 | 6/1983 | Richter et al. | 71/107 |
| 4,859,234 | 8/1989 | Alterman et al. | 71/103 |
| 4,963,690 | 10/1990 | Seele et al. | 548/264.8 |

Primary Examiner—Richard L. Raymond
Assistant Examiner—S. Mark Clardy
Attorney, Agent, or Firm—John W. Hogan, Jr.

[57] ABSTRACT

A herbicidal composition of an AHAS inhibiting herbicide and 1-carbethoxyethyl-3,6-dichloro-2-methoxybenzoate is safe for cereal crops and effective in controlling undesirable plant species.

11 Claims, No Drawings

HERBICIDAL COMPOSITION AND METHOD FOR SAFENING HERBICIDES IN CEREAL CROPS USING 1-CARBETHOXYETHYL-3,6-DICHLORO-2-METHOXYBENZOATE

BACKGROUND OF THE INVENTION

One of the most common practices for controlling undesirable plant species is the use of postemergent selective herbicides. For example certain AHAS inhibiting compounds are known herbicides which are effective against certain annual and perennial grass weeds. Unfortunately, these herbicides cannot be used in all crops, especially cereal crops such as corn, wheat and rice because the herbicide injures the crop as well as controlling the weeds.

Therefore what is needed in the art is a herbicide which is effective against weeds, while protecting the gramineous crop from injury.

SUMMARY OF THE INVENTION

A method for protecting cereal crops from injury caused by herbicidally effective amount of a herbicide which comprises applying an effective nonphytotoxic antidotal amount of 1-carbethoxyethy-3, 6-dichloro-2-methoxy benzoate to the seed of the crop, the foliage of the crop, or the soil surrounding the crop or crop seed is described. The invention also includes a safened herbicidal composition which is effective against weeds, but spares the crop.

DESCRIPTION OF THE INVENTION

The present invention relates to a method of safening herbicides by applying a chemical safener, 1-carbethoxyethyl-3,6-dichloro-2-methoxybenzoate, to the seed of the crop, the foliage of the crop or the soil surrounding the crop or crop seed. Herbicides which are suitable for use in the present invention include AHAS inhibiting herbicides or aryloxyphenoxy propionitrile herbicides. Preferred herbicides of the present invention include 1-[(o-acetylphenyl)sulfonyl]-3 -(4-methoxy-6-methyl-2-pyrimidinyl)urea, ethyl 3-{p-[3, 5-dichloro-2-pyridyl)oxy]phenoxy}-2-hydroxybutyronitrile carbonate, 5-ethyl-2-(4-isoproypyl-4-methyl-5-oxo -2-imidazolin-2-yl) nicotinic acid, 2-(4-isopropyl4-methyl-5-oxo-2-imidazolin-2-yl)-3-quinolinecarboxylic acid, and an isomeric mixture of methyl 6-(4-isopropyl-4 methyl-5-oxo-2-imidazolin-2-yl)-m-toluate and methyl 2-(4-isopropyl-4-methyl-5-oxo-2-imidazolin-2-yl)-p-toluate.

Although, many of these herbicides have been used with success in certain crops, they have been found to be phytotoxic in many cereal crops. Surprisingly, it has been found that by applying 1-carbethoxyethyl-3,6-dichloro-2-methoxybenzoate to the seed of the crop, the foliage of the crop or the soil surrounding the crop or crop seed the herbicide is safened.

The present invention also includes a safened herbicidal composition comprising a herbicide and the safener of the invention, 1-carbethoxyethyl-3, 6-dichloro-2-methoxybenzoate.

Safening of cereal crops such as corn, wheat and rice, from the post emergence application of herbicides may be effected by allowing said crop plants to grow until the third to early fourth leaf stage then spraying with an aqueous solution of the safener either alone or tank mixed with at least one of the above described herbicides. The tank mix should contain effective amounts of herbicide and effective amount of the safener. Although rates will naturally vary with the particular herbicide and crop, typical rates of application for the safener are about 0.063 kg/ha to 2.0 kg/ha.

The present invention may also be practiced by applying the herbicide and/or safener to the soil pre-emergence. A tank mix of the safener and herbicide may be conveniently prepared and employed or sequential sprayings may be used in accordance with the present method.

A wide variety of troublesome weed species can also be effectively controlled in the presence of important agronomic crops such as corn, wheat and rice, by safening the crop plants by any conventional seed treatment techniques or by uniformly coating the seeds with a 5% to 50% wettable powder composition of the safener, planting the coated seed in the usual manner, and spraying the soil with a herbicide such as 1-[(0-acetylphenyl)-sulfonyl]-3-(4-methoxy-6-methyl-2pyrimidinyl)urea, an isomeric mixture of methyl 6-(4-isopropyl-4-methyl-5-oxo-2-imidazolin-2-yl)-m-toluate and methyl 2-(4-isopropyl-4-methyl-5-oxo-2-imidazolin -2-yl)-p-toluate, 5-ethyl-2-(4-isopropyl-4-methyl -5-oxo-2-imidazolin-2-yl)nicotinic acid, 2-(4-isopropyl -4-methyl-5-oxo-2-imidazolin-2-yl)-3-quinolinecarboxylic acid or by incorporating the herbicide into the soil before the coated seeds have been planted.

In order to facilitate a more complete understanding of the invention the following examples are presented primarily for the purpose of illustrating more specific details thereof. The invention is not to be limited thereby except as defined in the claims.

EXAMPLE 1

Evaluation of 1-carbethoxyethyl-3,6-dichloro-2-methoxy benzoate as a Safener for Wheat Injury from Preemergence Applications of the Sulfamoylurea Herbicide 1-[(o-acetylphenyl)sulfonyl]-3-(4-methoxy-6-methyl-2-pyrimidinyl)urea Wheat seeds (var. Wakooma) are planted in sterilized soil. The soil surface is moistened and sprayed preemergence with a formulation of 1-[(o-acetylphenyl)sulfonyl]-3-(4-methoxy-6-methyl-2-pyrimidinyl)urea containing 32 g/1 of active ingredient, or 1-[(o-acetylphenyl)sulfonyl]-3-(4-methoxy-6-methyl -2-pyrimidinyl)urea mixed with various rates of a formulation of 1-carbethoxyethyl-3,6-dichloro-2-methoxy benzoate containing 160 g/1 of active ingredient. The herbicide and safener are diluted with water to provide the equivalent of 0.05 Kg per hectare (Kg/Ha) of herbicide, and 0.0625 - 2.0 Kg/Ha of safener to the soil surface when applied though a spray nozzle operating at 40 psi for a predetermined time. Pots are then placed on greenhouse benches, watered and cared for in accordance with conventional greenhouse procedures.

From 2-4 weeks after treatment, the tests are terminated and each pot is examined and rated by measuring the height of the foliage. The test results are averaged and expressed as a percent growth reduction compared to an untreated check, using the following formula:

% Growth Reduction =

$$100 - \left[ \frac{\text{Height of Treatment Plants}}{\text{Height of Untreated Plants}} \times 100 \right]$$

the results are shown in Table I in which compound A is 1-[(0-acetylphenyl)sulfonyl]-3-(4-methoxy-6-methyl-2pyrimidinyl)urea and B is 1-carbethoxyethyl-3, 6-dichloro -2-methoxy benzoate.

TABLE I

| TREATMENT | RATE (Kg/Ha) | % GROWTH REDUCTION |
|---|---|---|
| Untreated Check | 0 | 0 |
| A | 0.05 | 67 |
| A + B | 0.05 + 0.063 | 25 |
| A + B | 0.05 + 0.125 | 36 |
| A + B | 0.05 + 0.25 | 27 |
| A + B | 0.05 + 0.50 | 29 |
| A + B | 0.05 + 0.75 | 27 |
| A + B | 0.05 + 1.0 | 24 |
| A + B | 0.05 + 2.0 | 32 |

Shoot height of the untreated check was 39.2 cm

EXAMPLE 2

Evaluation of 1-carbethoxyethyl-3,6-dichloro-2-methoxybenzoate as a Safener for Wheat Injury from Postemergence Applications of the Sulfamoylurea Herbicide 1-[(o-acetylphenyl)sulfonyl]-3-(4-methoxy-6-methyl-2-pyrimidinyl)urea Wheat seeds (var. Wakooma) are planted in sterilized loamy sand soil containing 5% organic matter. Plants are sprayed with a formulation of 1-[(o-acetylphenyl)-sulfonyl]-3-(4-methoxy-6-methyl-2pyrimidinyl)urea containing 32 g/1 of active ingredient, or 1-[(o-acetyl-phenyl)sulfonyl]-3-(4-methoxy -6-methyl-2-pyrimidinyl)urea mixed with various rates of a formulation of 1-carbethoxyethyl-3,6-dichloro -2-methoxybenzoate containing 160 g/1 of active ingredient. The herbicide and safener are diluted with water to provide the equivalent of 0.10 Kg per hectare (Kg/Ha) of herbicide, and 0.0625 - 2.0 Kg/Ha of safener to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2-4 weeks after treatment, the tests are terminated and each pot is examined and rated by measuring the height of the foliage. The test results are averaged and expressed as a percent growth reeduction compared to an untreated check, as described in Example 1.

The results are shown in Table II in which compound A is 1-[(o-acetylphenyl)sulfonyl]-3-(4-methoxy -6-methyl-2-pyrimidinyl)urea and B is 1-carbethoxyethyl -3,6-dichloro-2-methoxybenzoate.

TABLE II

| TREATMENT | RATE (Kg/Ha) | % GROWTH REDUCTION |
|---|---|---|
| Untreated Check | 0 | 0 |
| A | 0.1 | 34 |
| A + B | 0.1 + 0.063 | 25 |
| A + B | 0.1 + 0.125 | 29 |
| A + B | 0.1 + 0.25 | 15 |
| A + B | 0.1 + 0.50 | 18 |
| A + B | 0.1 + 0.75 | 20 |
| A + B | 0.1 + 1.0 | 11 |
| A + B | 0.1 + 2.0 | 18 |

Shoot height of the untreated check was 43.3 cm

EXAMPLE 3

Evaluation of 1-carbethoxyethyl-3,6-dichloro-2-methoxybenzoate Applied to the Foliage as a Safener for Postemergence Applications of an isomeric mixture of methyl 6-(4-isopropyl-4-methyl-5-oxo-2-imidazolin-2-yl) -m-toluate and methyl 2-(4-isopropyl-4-methyl-5-oxo2 -imidazolin-2-yl)-p-toluate Wheat seeds (var. Wakooma) are planted in sterilized loamy sand soil containing 5% organic matter. Plants are sprayed with a formulation of an isomeric mixture of methyl 6-(4-isopropyl-4-methyl-5 -oxo-2-imidazolin-2-yl)-m-toluate and methyl 2-(4-isopropyl -4-methyl-5-oxo-2-imidazolin-2-yl)-p-toluate containing 300 g/1 of active ingredient, or an isomeric mixture of methyl 6-(4-isopropyl-4-methyl-5-oxo -2-imidazolin-2-yl)-m-toluate and methyl 2-(4-isopropyl -4-methyl-5-oxo-2-imidazolin-2-yl)-p-toluate mixed with various rates of a formulation of 1-carbethoxyethyl -3,6-dichloro-2-methoxybenzoate containing 160 g/1 of active ingredient. The herbicide and safener are diluted with water to provide the equivalent of 0.8 Kg/Ha of herbicide, and 0.0625 - 2.0 kg/ha of safener to the foliage when applied through a spray nozzle operating at 40 psi for a predetermined time. The herbicide spray solution contains 0.25% of the spray adjuvant Igepal DM-710, a dinonyl-phenoxypoly(ethylene-oxy) ethanol non-ionic wetting agent. Pots are then placed on greenhouse benches, watered and cared for in accordance with conventional greenhouse procedures. From 2-4 weeks after treatment, the tests are terminated and each pot is examined and rated by measuring the height of the foliage. The test results are averaged and expressed as a percent growth reduction compared to an untreated check, as described in example 1.

The results are shown in Table III in which compound B is 1-carbethoxyethyl-3,6-dichloro-2 -methoxybenzoate and C is an isomeric mixture of methyl 6-(4-isopropyl-4-methyl-5-oxo-2-imidazolin-2-yl) -m-toluate and methyl 2-(4-isopropyl-4-methyl-5-oxo -2-imidazolin-2-yl)-p-toluate.

TABLE III

| TREATMENT | RATE (Kg/Ha) | % GROWTH REDUCTION |
|---|---|---|
| Untreated Check | 0 | 0 |
| C | 0.8 | 25 |
| C + B | 0.8 + 0.063 | 13 |
| C + B | 0.8 + 0.125 | 6 |
| C + B | 0.8 + 0.25 | 9 |
| C + B | 0.8 + 0.50 | 3 |
| C + B | 0.8 + 0.75 | 11 |
| C + B | 0.8 + 1.0 | 3 |
| C + B | 0.8 + 2.0 | 7 |

Shoot height of the untreated check was 43.3 cm

EXAMPLE 4

Evaluation of 1-carbethoxyethyl-3,6-dichloro-2-methoxybenzoate Applied as a Seed Treatment for Imidazolinone Herbicide Injury to Corn Corn seeds (Pioneer 3475) are treated with the safener 1-carbethoxyethyl-3,6-dichloro-2-methoxybenzoate by first making a stock solution of 25 milligrams of the safener in 2.5 milliliters of an acetone: dimethylformamide (10:1) mixture. Aliquots of the stock solution ranging from 50 microliters to 400 microliters are added to 2 grams of corn seed and shaken thoroughly to provide seed treatment rates equivalent to 0.25 –4.0 milligrams per gram of seed. Seeds are dried, then planted in artificial growth medium METROMIX 350, a mixture of Canadian peat moss, domestic horticultural vermiculite, processed bark ash, washed granite sand and a wetting agent. Seeds are incubated overnight in plastic humidity chambers prior to herbicide treatment. 5-ethyl-2-(4-isopropyl-4-methyl-5-oxo-2-imidazolin-2-yl)nicotinic acid (240 mg/ml active ingredient) is applied by subirrigation as a single treatment at 0.75 ppm in water. Flats are placed on greenhouse benches, watered and cared for in accordance with conventional greenhouse procedures. From 7–10 days after treatment, the tests are terminated and each flat is examined and rated by measuring the height of the foliage. The test results are averaged and expressed as a percent growth reduction compared to an untreated check, as described in Example 1.

The results are shown in Table IV in which compound B is 1-carbethoxyethyl-3,6-dichloro-2-methoxybenzoate and D is 5-ethyl-2-(4-isopropyl-4-methyl-5-oxo-2-imidazolin-2-yl)nicotinic acid.

TABLE IV

| TREAT-MENT | RATE HERBICIDE (PPM) | RATE SAFENER (MG/G SEED) | % GROWTH REDUCTION |
| --- | --- | --- | --- |
| Untreated Check | 0 | 0 | 0 |
| D | 0.75 | 0 | 52 |
| D + B | 0.75 | 0.25 | 46 |
| D + B | 0.75 | 0.50 | 46 |
| D + B | 0.75 | 1.0 | 39 |
| D + B | 0.75 | 2.0 | 44 |
| D + B | 0.75 | 4.0 | 27 |

Shoot height of the untreated check was 29.7 cm

EXAMPLE 5

Evaluation of 1-carbethoxyethyl-3,6-dichloro-2-methoxybenzoate Applied to the Foliage as a Safener for Postemergence Applications of the Imidazolinone Herbicides Imazaquin and Imazethapyr Corn seeds (Pioneer 3475) are planted in sterilized loamy sand soil containing 5% organic matter. Plants are sprayed when they have reached the 2–4 leaf stage of growth. Commercial formulations of the herbicides imazaquin and imazethapyr, and the safener 1-carbethoxyethyl-3,6-dichloro-2-methoxybenzoate, are diluted with water to provide the equivalent of 0.01 and 0.05 kg/ha respectively of herbicide, and 0.125–0.5 kg/ha of safener to the foliage when applied through a spray nozzle operating at 40 psi for a predetermined time. The spray solution contains 0.25% of the spray adjuvant CHARGER E, an alkylaryl polyethoxyethanol and N-butanol 80% non-ionic wetting agent manufactured by Blue Ribbon Products Co. Pots are placed on greenhouse benches, watered and cared for in accordance with conventional greenhouse procedures.

From 2–4 weeks after treatment, the tests are terminated and each pot is examined and rated by measuring the height of the foliage. The test results are averaged and expressed a percent growth reduction compared to an untreated check, as described in example 1.

The results are shown in Table V in which compound B is 1-carbethoxyethyl-3,6-dichloro-2-methoxybenzoate, D is 5-ethyl-2-(4-isopropyl-4-methyl-5-oxo-2-imidazolin-2-yl)nicotinic acid ("imazethapyr") and E is 2-(4-isopropyl-4-methyl-5-oxo-2-imidazolin-2-yl)-3-quinolinecarboxylic acid ("imazaquin").

TABLE V

| TREATMENT | RATE (Kg/Ha) | % GROWTH REDUCTION |
| --- | --- | --- |
| Untreated Check | 0 | 0 |
| E | 0.01 | 20 |
| E + B | 0.01 + 0.125 | 12 |
| E + B | 0.01 + 0.25 | 5 |
| E + B | 0.01 + 0.50 | 6 |
| D | 0.05 | 44 |
| D + B | 0.05 + 0.125 | 27 |
| D + B | 0.05 + 0.25 | 23 |
| D + B | 0.05 + 0.50 | 21 |

Shoot height of the untreated check was 74.2 cm

EXAMPLE 6

Evaluation of 1-carbethoxyethyl-3,6-dichloro2-methoxybenzoate Applied to the Foliage as a Safener for Postemergence Applications of the Aryloxyphenoxy-propionitrile Herbicide ethyl 3-{p-[(3,5-dichloro-2-pyridyl)oxy]phenoxy}-2-hydroxybutyronitrilecarbonate Rice (var. Tebonnet) seeds are planted in sterilized loamy sand soil containing 5% organic matter. Plants are sprayed when they have reached the 2–4 leaf stage of growth. A IEC (120 g/l) formulation of ethyl 3-{p[(3,4-dichloro-2-pyridy)oxy]phenoxy}-2hydroxybutyronitrilecarbonate, and the safener 1-carbethoxyethyl-3,6-dichloro-2-methoxybenzoate (160 g/l), are diluted with water to provide the equivalent of 0.5 and 0.75 Kg per hectare (kg/ha) of herbicide, and 0.025–0.5 kg/ha of safener to the foliage when applied through a spray nozzle operating at 40 psi for a predetermined time. The spray solution contains 0.25% of the spray adjuvant TRITON X-100, a non-ionic wetting agent. Pots are placed on greenhouse benches, watered and cared for in accordance with conventional greenhouse procedures. From 2–4 weeks after treatment, the tests are terminated and each pot is examined and rated by measuring the height of the foliage. The test results are averaged and expressed as a percent growth reduction compared to an untreated check, as described in example 1.

The results are shown in Table VI in which compound B is 1-carbethoxyethyl-3,6-dichloro-2-methoxybenzoate and F is ethyl 3-{p-[(3,5-dichloro-2-pyridyl)oxy][henoxy}-2-hydroxybutyronitrilecarbonate.

TABLE VI

| TREATMENT | RATE (Ka/Ha) | % GROWTH REDUCTION |
| --- | --- | --- |
| Untreated Check | 0 | 0 |
| F | 0.5 | 36 |
| F + B | 0.5 + 0.025 | 19 |
| F + B | 0.5 + 0.05 | 18 |
| F + B | 0.5 + 0.075 | 21 |

TABLE VI-continued

| TREATMENT | RATE (Kg/Ha) | % GROWTH REDUCTION |
|---|---|---|
| F + B | 0.5 + 0.1 | 29 |
| F + B | 0.5 + 0.25 | 11 |
| F + B | 0.5 + 0.5 | 26 |
| F | 0.75 | 51 |
| F + B | 0.75 + 0.025 | 35 |
| F + B | 0.75 + 0.05 | 29 |
| F + B | 0.75 + 0.075 | 26 |
| F + B | 0.75 + 0.1 | 12 |
| F + B | 0.75 + 0.25 | 51 |
| F + B | 0.75 + 0.5 | 23 |

Shoot height of the untreated check was 43.3 cm

What is claimed is:

1. A method for protecting cereal crops from injury caused by a herbicidally effective amount of a herbicide which comprises applying an effective non-phytotoxic antidotal amount of 1-carbethoxyethyl-3, 6-dichloro-2-methoxybenzoate to the crop plant, the seed of the crop, or the soil surrounding the crop or crop seed.

2. The method according to claim 1 wherein the herbicide is an AHAS inhibiting herbicide.

3. The method according to claim 1 wherein the herbicide is an aryloxyphenoxy propionitrile herbicide.

4. The method according to claim 1, wherein the herbicide is selected from the group consisting of 1-[(o-acetylphenyl)sulfonyl]-3-(4-methoxy-6-methyl-2-pyrimidinyl) urea, ethyl 3-{p-[(3,5-dichloro-2pyridyl)oxy]phenoxy}-2-hydroxybutyronitrilecarbonate, an isomeric mixture of methyl 6-(4-isopropyl-4-methyl5-oxo-2-imidazolin-2-yl)-m-toluate and methyl 2-(4-isopropyl -4-methyl-5-oxo-2-imidazolin-2-yl)p-toluate, 5-ethyl-2-(4-isopropyl-4-methyl-5oxo-2-imidazolin-2-y-1) -nicotinic acid, and 2-(4-isopropyl-4-methyl-5-oxo-2-imidazolin -2-yl)-3-quinolinecarboxylic acid.

5. The method according to claim 1, wherein the crop is wheat, rice or corn.

6. The method according to claim 1, wherein the 1-carbethoxyethyl-3,6-dichloro-2-methoxybenzoate is applied to the foliage of the crop.

7. The method according to claim 1, wherein the herbicide is 5-ethyl-2-(4-isopropyl-4-methyl-5-oxo2-imidazolin-2-yl)nicotinic acid, the crop is corn and the 1-carbethoxyethyl-3,6-dichloro-2-methoxybenzoate is applied to the corn seed.

8. The method according to claim 1, wherein the crop is wheat and the herbicide is an isomeric mixture of methyl 6-(4-isopropyl-4-methyl-5-oxo-2-imidazolin -2-yl)-m-toluate and methyl 2-(4-isopropyl-4-methyl -5-oxo-2-imidazolin-2-yl)-p-toluate or 1-[(0-acetylphenyl) sulfonly]-3-(4-methoxy-6-methyl-2pyrimidinyl)urea.

9. The method according to claim 1, wherein the crop is corn and the herbicide is 5-ethyl-2-(4-isopropyl -4-methyl-5-oxo-2-imidazolin-2-yl)nicotinic acid 10. The method according to claim 1, wherein the crop is rice and the herbicide is ethyl 3-{p-[(3,5-dichloro -2-pyridyl)oxy]phenoxy}-2-hydroxybutyronitrilecarbonate.

11. A safened herbicidal composition comprising a herbicidally effective amount of a herbicide selected from the group consisting of 1[(0-acetylphenyl)-sulfonyl]-3-(4-methoxy-6-methyl-2pyrimidinyl)urea, ethyl 3-{p-[(3,5-dichloro-2pyridyl)oxy]phenoxy}-2-hydroxybutyronitrilecarbonate, an isomeric mixture of methyl 6-(4-isopropyl-4-methyl-5 -oxo-2-imidazoline-2-yl)-m-toluate and methyl 2-(4-isopropyl -4-methyl-5-oxo-2-imidazolin-2-yl)-p-toluate, 5-ethyl-2-(4-isopropyl-4-methyl-5-oxo-2-imidazolin-2yl) nicotinic acid and 2-(4-isopropyl-4-methyl-5-oxo-2-imidazolin -2-yl)-3-quinolinecarboxylic acid and an effective non-phytotoxic antidotal amount of 1-carbethoxyethyl -3,6-dichloro-2-methoxybenzoate.

* * * * *